United States Patent
Burgeson et al.

(10) Patent No.: US 6,685,929 B2
(45) Date of Patent: Feb. 3, 2004

(54) VISCOUS SCENT LURE FOR HUNTING

(76) Inventors: John R. Burgeson, 1050 McKinley St., Anoka, MN (US) 55303; Brian Burgeson, 3759 New Brighton Rd., Arden Hills, MN (US) 55112

( * ) Notice: Subject to any disclaimer, the term of this patent is extended or adjusted under 35 U.S.C. 154(b) by 0 days.

(21) Appl. No.: 10/037,675

(22) Filed: Jan. 2, 2002

(65) Prior Publication Data

US 2003/0124089 A1 Jul. 3, 2003

(51) Int. Cl.⁷ .......................... A01N 63/00; A01N 25/24
(52) U.S. Cl. .......................... 424/84; 424/405; 424/407; 424/484; 424/485; 424/486; 424/488; 424/545
(58) Field of Search .......................... 424/545, 84, 405, 424/407, 484, 485, 486, 488

(56) References Cited

U.S. PATENT DOCUMENTS

| | | |
|---|---|---|
| 4,472,377 A | 9/1984 | Teranishi et al. |
| 4,944,940 A | 7/1990 | Christenson, II |
| 5,327,667 A | 7/1994 | Fore |
| 5,415,862 A | 5/1995 | Bethshears et al. |
| 5,565,111 A | 10/1996 | Newman |
| 5,698,111 A | 12/1997 | Newman |
| 5,738,851 A | 4/1998 | Colavito |
| 5,916,551 A | 6/1999 | Newman |
| 5,916,552 A | 6/1999 | Perry |
| 6,149,901 A | 11/2000 | Weiser |
| 6,153,230 A | 11/2000 | Corley, Jr. |
| 6,165,570 A | 12/2000 | Shannon |
| 6,231,849 B1 * | 5/2001 | Schiller .......................... 424/84 |

OTHER PUBLICATIONS

Tink's 2001 Hunting Products Catalog, p. 2 (2001).
"Scent Elimination Products for the Hunter", Robinson Laboratories, Inc., 2001/2002, p. 18.
"A Formulator's Guide to Methocel Cellulose Ethers in Personal Care Products", Dow Chemical Company, Jun., 1999.
"Methocel Personal Care Products", Dow Chemicals web site, retrieved from Internet Nov. 19, 2001.

* cited by examiner

*Primary Examiner*—John Pak
(74) *Attorney, Agent, or Firm*—Gerald E. Helget; Nelson R. Capes; Briggs and Morgan

(57) ABSTRACT

A viscous, non-liquid, non-gel scent lure for hunting, consisting of animal urine and a thickening agent. The thickening agent may comprise about 1% to about 7% by weight. The resulting viscosity of the solution ranges from about 1500 to about 10,000 centipoise.

6 Claims, 1 Drawing Sheet

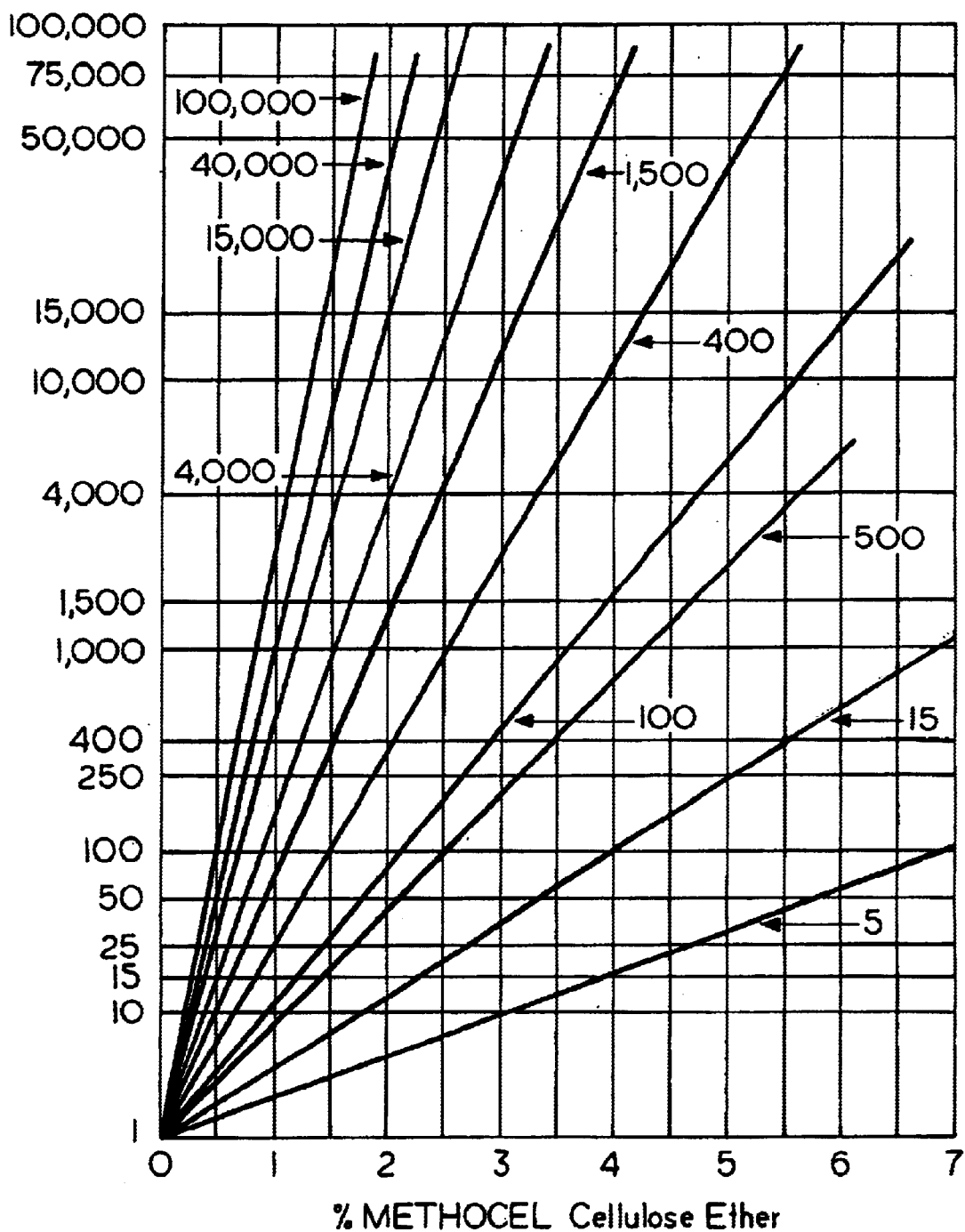

VISCOUS SCENT LURE FOR HUNTING

BACKGROUND OF THE INVENTION

The present invention relates to a viscous scent lure for hunting, and in particular to a scent lure that is a non-liquid and a non-gel.

A number of liquid scent lures are known. However, liquid scent lures generally do not work well. First, they do not stick well to smooth surfaces, but instead tend to run off. Second, it is difficult to apply the scent in a thick layer. Because thick layers cannot be applied, the scent has a tendency to evaporate quickly. Third, liquid scents are easily washed off by rainfall. Fourth, it is difficult to control application of a liquid scent, especially the application of large volumes.

Likewise, a number of gel scent lures are also known. However, these lures also have a number of problems. First, some gels do not evaporate well: the molecules of scent that are below the surface layer can remain trapped, resulting in less scent being dispersed. Second, gels generally cannot be used on wick material, such as is sometimes used in scent applicators. Third, gels are not flowable, so they do not spread out over anything but the immediate area of application. Fourth, they are sometimes difficult to dispense from bottles. Fifth, some gels contain large amounts of inert material to create the gel, so they do not contain as much actual volume of scent molecules. Sixth, gels do not penetrate into tight crevices, such as small, tight tree crotches, cracks in dry tree knots, and cracks in dead and weathered branches where the bark has fallen off.

There is a need for a viscous, non-liquid, non-gel scent lure that addresses the above problems.

SUMMARY OF THE INVENTION

1. A viscous, non-liquid, non-gel scent lure for hunting, comprising:
   a) animal urine; and
   b) a thickening agent;
   c) wherein the viscosity of the lure is in the range of about 1500 to about 10,000 centipoise.

BRIEF DESCRIPTION OF THE DRAWINGS

FIG. 1 is a graph of viscosity vs. concentration for Dow Methocel thickening agent.

DETAILED DESCRIPTION OF THE PREFERRED EMBODIMENT

The viscous, non-liquid, non-gel scent lure of the present invention 10 comprises an animal urine 20 and a thickening agent 30.

The following table shows the expected characteristics of materials with varying viscosity numbers (centipoise):

| Viscosity (centipoise) | Characteristics |
| --- | --- |
| 0–500 | Thin liquid; flows easily and drips |
| 1500–10,000 | Medium viscosity. Liquid flows with little difficulty. Little to low drip potential. |
| 55,000–100,000 | A gel. Will flow very slowly and will spread under pressure |
| >100,000 | Very thick gels |

In order to produce a scent lure with the desired characteristics, the viscosity of the scent lure should be in the range of about 1500 centipoise to about 10000 centipoise. Most preferably, the viscosity should be about 4000 centipoise.

FIG. 1 shows that various viscosities can be obtained by combining various concentrations of several different Dow Methocel cellulose ethers as thickening agents. For example, a 2% concentration of Dow Methocel 4000 would produce a solution with a viscosity of about 4000 centipoise. Source: Dow Methocell Cellulose Ether Technical Handbook, p. 19, June, 1997.

The scent lure 10 can be made by combining animal urine 10 with about 1% to about 7% by weight of thickening agent 30.

A number of materials can be used as the thickening agent 30. One group of possible materials consists of methylcellulose and hydroxypropylmethylcellulose. These polymers are available from the Dow Chemical Co. as METHOCEL cellulose ether products.

Another group of possible materials consists of methylcellulose, hydroxypropylmethylcellulose, hydroxyethylcellulose, hydroxypropylcellulose, cellulose gum, carboxymethylhydroxycellulose, 1-vinyl-pyrolidone, carboxypolymethylene acrylic derivative polymers, magnesium aluminum silicate, and carbohydrate gums and derivatives. Hydroxypropylmethylcellulose is available as Prima-Flow MP 3295A Benecel from Aqualon/Hercules, Inc., Wilmington, Del. Hydroxyethylcellulose is available as the Natrosol Series from Aqualon/Hercules, Inc. Hydroxypropylcellulose is available as Klucel from Aqualon/Hercules, Inc. Cellulose gum is available as Aqualon CMC from Aqualon/Hercules, Inc. Carboxymethylhydroxycellulose is available as Aqualon CMC-sodium slat from Aqualon/Hercules, Inc. 1-vinyl-2-pyrolidone is available as PVP K-Series and Plastodone Series from International Specialty Products, Inc., Wayne, N.J. Carboxypolymethylene acrylic derivative polymers are available as the Carbopol/Ultrex series from B F Goodrich/Noveon, Inc., Cleveland, Ohio. Magnesium aluminum silicate is available from the R. T. Vanderbilt Co., Inc., Norwalk, Conn. Carbohydrate gums and derivatives are available from Gumix International, Inc., Fort Lee, N.J.

In one embodiment, thickening agent (Dow Methocel 4000) in the amount of 0.28 g. to 2 g. was dissolved in 1 oz. of animal urine (preferably female deer urine). This produces a solution containing 1% to 7% of thickening agent (1 g.=0.035 oz.). Optimally, 0.57 g of Dow Methocell 4000 is dissolved in 1 oz. of animal urine. This produced a scent lure which was thick enough to sling to smooth surfaces and which would not readily wash away in the rain. At the same time, the scent lure was thin enough that it evaporated well, penetrated wick material effectively, flowed slowly out of a bottle, adhered well to surfaces, and could penetrate into tight crevices. If the viscosity of the scent lure were to be measured, it is believed that it would be about 4000 centipoise.

Other combinations of Dow Methocel family cellulose ethers may be used, and if the viscosity of the resulting scent lure were to be measured, it is believed that the viscosity would be in the range of about 1500 centipoise to about 10000 centipoise.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A viscous, non-liquid, non-gel scent lure for hunting, consisting essentially of:
   a) animal urine; and
   b) about 1% to about 7% by weight of a thickening agent selected from the group consisting of methylcellulose, hydroxypropylmethylcellulose, hydroxyethylcellulose, hydroxypropylcellulose, cellulose gum, carboxymethylhydroxycellulose, 1-vinyl-2-pyrrolidone, carboxypolymethylene acrylic derivative polymers, magnesium aluminum silicate, and carbohydrate gums and derivatives;
   c) wherein the viscosity of the lure is about 4000 centipoise.

2. The scent lure of claim 1, wherein the animal urine is female deer urine.

3. The scent lure of claim 1, wherein the thickening agent comprises about 2% by weight.

4. A viscous, non-liquid, non-gel scent lure for hunting, consisting essentially of;
   a) animal urine; and
   b) about 1% to about 7% by weight of a thickening agent selected from the group consisting of methylcellulose and hydroxypropylmethylcellulose;
   c) wherein the viscosity of the lure is about 4000 centipoise.

5. The scent lure of claim 4, wherein the animal urine is female deer urine.

6. The scent lure of claim 4, wherein the thickening agent comprises about 2% by weight.

* * * * *